United States Patent [19]

Milne

[11] Patent Number: 5,413,113

[45] Date of Patent: May 9, 1995

[54] ELECTRONIC ALLEGRO-SENSITIVITY TEST DEVICE

[76] Inventor: Robert D. Milne, 2432 Greens Ave., Henderson, Nev. 89014

[21] Appl. No.: 215,358

[22] Filed: Mar. 21, 1994

[51] Int. Cl.⁶ .............................................. A61M 37/00
[52] U.S. Cl. .................................... 128/734; 123/743
[58] Field of Search ....................... 128/739, 736, 743; 604/19, 20

[56] References Cited

U.S. PATENT DOCUMENTS

| | | | |
|---|---|---|---|
| 2,308,933 | 1/1943 | Raesler | 128/734 X |
| 4,494,544 | 1/1985 | Van Dyke et al. | 128/734 |
| 4,809,707 | 3/1989 | Kraft et al. | 128/743 X |
| 4,819,657 | 4/1939 | Kraft et al. | 128/743 X |
| 5,246,008 | 9/1993 | Mueller | 128/734 X |

Primary Examiner—Sam Rimell
Attorney, Agent, or Firm—Michael I. Kroll

[57] ABSTRACT

A device and method for testing a patient's sensitivity to a plurality of potential allergens is disclosed using the galvanometric skin response of the patient's body to determine the same. A pair of electrodes are attached at separate locations of the body and are connected to a signal amplification unit and A/D converter, which is in turn connected to the bus of a personal computer. An allergen sampling tray is also connected to the computer bus and also a third electrode adapted to deliver the allergen samples in sequence transcutaneously. The skin response changes according to severity of the allergen reaction, and the signal amplification means and A/D converter allow these changes to be viewed graphically in a real time mode on the computer screen and also to be stored within the computer and to be printed out to allow the physician and the patient a hard copy of the test data.

4 Claims, 3 Drawing Sheets

ELECTRONIC ALLEGRO-SENSITIVITY TEST DEVICE

CROSS REFERENCE TO RELATED DISCLOSURE DOCUMENT

This invention was disclosed in Information Disclosure Document No. 332,087, filed with the United States Patent and Trademark Office on Jun. 7, 1993.

BACKGROUND OF THE INVENTION

1. Field of the Invention

The present invention relates to allergen testing. More specifically, it relates to a device for allergen testing that includes a pair of sensing electrodes, an allergen delivery electrode connected to an allergen sample tray, a microprocessor for amplifying and comparing the signals from the two sensing electrodes, an A/D converter for turning the amplified data to a digital information stream, and an interface including software to display and store the gathered information on a conventional personal computer (PC).

2. Description of the Prior Art

Presently, allergy testing commonly takes the form of introducing allergens to a portion of the patients' dermis and then measuring the size and color of the induced weal. This often involves breaking the surface of the skin to introduce the substance and has a number of drawbacks. It is painful, for one, and the patient can have a severe reaction if they are extremely sensitive to one of the introduced substances. Additionally, the procedure causes some discomfort. Another prior art method of testing involves introducing the potential allergen and then measuring the temperature response, by means of electrodes or the other sensing means, of the skin proximate the area where the substance was introduced. This allows for smaller amounts of the allergen to be used, but in many cases it still involves the breaking of the skin. The present invention attempts to improve on these prior art methods and devices by using galvanometric skin response to determine the sensitivity of the patient to various substances. As will be seen, the simplicity and effectiveness of my invention is not rivaled in the prior art.

There have been a number of U.S. Patents issued that relate to this art that were uncovered during a search, and they are hereinafter discussed:

U.S. Pat. No. 4,702,259, issued on Oct. 27, 1987 to Marc Ferreira et al., discloses a device for measuring and indicating changes in the electrical resistance of a living body. The device includes an analog portion, a digital portion and a stable source of power for both portions. The analog portion includes a bridge network which includes a potentiometer, which turns together with the potentiometer provided in the digital portion, and digital processing circuitry. Digital displays determine and display a count indicative of the position of the potentiometer and the total amount of rotation of said potentiometer. In addition, a computer may be interfaced with the device to record or play back the changes in the resistance of the living body. Unlike the present invention, there is nowhere in the document a teaching or disclosure that discusses using the apparatus as a testing device for allergen response, nor is there any type of delivery system for stimuli disclosed.

U.S. Pat. No. 4,805,621 issued to Roland Heinze et al. on Feb. 21, 1989 discloses an apparatus for measuring the impedance of body tissue with a signal source connected to the tissue to be measured which supplies an electrical signal to the tissue, a unit for acquiring an impedance signal from the body tissue dependent on the electrical signal, and a evaluation stage for the impedance signal. The evaluation stage filters out low frequency signal components corresponding to the conductance of the tissue, and has a signal output to which the signal components which were filtered out are supplied. In this device, an electrical signal is impressed on the tissue of the patient through a pair of electrodes and the voltage drop is measured. This is unlike the present invention, which measures the galvanometric skin response in the presence of allergenic substances and displays the same.

Next in this discussion is U.S. Pat. No. 4,809,707 issued to Thomas L. Kraft et al. on Mar. 7, 1989. Kraft et al. show an electrode for performing a plurality of allergy tests on a patient undergoing tests. The allergy electrode consists of a plurality of individual testing electrodes and a single common electrode. Each of the testing electrodes includes allergen delivery apparatus and a temperature sensor. The allergen is contained in a removable allergen impregnated pad. If a dry allergen is used, it may be hydrolized with a drop of distilled water prior to application. A small electric charge charges a charge plate on one side of the allergen pad and a common ring on the electrodes is grounded in a circuit with the charging plate, thereby causing electric field to transfer the allergen through the pores of the skin. The area surrounding the allergen delivery area is sensed for temperature by a thin film temperature sensor and a rigid temperature conducted base. A thermistor or other temperature to voltage transducer converts the sensed temperature to an electric voltage which is applied through appropriate differential amplifiers and multiplexer to an analog to digital converter. The digital data is then stored by a microprocessor in random access memory. An output device can be connected to receive the stored data and the time at which it was stored so as to manifest to the physician the change in temperature of the tested area with respect to time. This discloses an electrode for non-invasive allergy testing. Included are plurality of testing electrodes and a common electrode. Each of the testing electrodes have therein an allergen impregnated pad, a charge plate, a common ring grounded in the circuit with the charge plate, and a thin film temperature sensor or the like. A small charge is placed on the charge plate, which causes the allergen to transfer through the pores of the skin, while the thin film sensors monitor temperature in the proximate area. The common electrode monitors temperature in a distant area. Processing and storage means are disclosed to allow the physician to review the results of the test.

Lastly, U.S. Pat. No. 4,819,657 issued on Apr. 11, 1989, also to Thomas L. Kraft et al. discloses a automatic allergy detection system. The system includes an electrode capable of testing up to eight different allergies and an associated electronic unit. The electrode includes apparatus to transcutaneously deliver an allergen to the patient without puncturing the patient's skin. The electrode also includes a temperature sensor for sensing the skin temperature in the area surrounding the deliver of the allergen. Electronic apparatus is provided for processing the sensed temperature and storing data related thereto for subsequent print out to an output device. The allergy testing system is controlled so that periodic temperature readings are made at thirty second intervals over approximately a fifteen minute testing span. The data can be printed out in a graphic format to allow the physician to easily and quickly make more accurate diagnosis. In this device there are disclosed electrodes similar to those discussed in Kraft et al. ('707). However, more detail is gone into concerning the processing and data storage portion of the device. Neither of the two Kraft et al. patents discusses the use of galvanometric skin response as a method of ascertaining a patients sensitivity to a specific substance.

None of the above inventions and patents, taken either singly or in combination, is seen to describe the instant invention as claimed.

SUMMARY OF THE INVENTION

The present invention is a device for testing a patient's sensitivity to a plurality of potential allergens by using the galvanometric skin response of the patient's body to determine the same. A pair of electrodes are attached at separate locations of the body and are connected to a signal amplification unit and A/D converter, which is in turn connected to the bus of a personal computer. An allergen sampling tray is also connected to the computer bus and also a third electrode adapted to deliver the allergen samples in sequence transcutaneously. The skin response changes according to severity of the allergen reaction, and the signal amplification means and A/D converter allow these changes to be viewed graphically in a real time mode on the computer screen and also to be stored within the computer and to be printed out to allow the physician and the patient a hard copy of the test data.

Accordingly, it is a principal object of the invention to provide a new and improved galvanic skin response allergen testing device which overcomes the disadvantages of the prior art in a simple but effective manner.

It is another principal object of the invention to provide an allergen testing device using galvanometric skin response that allows the patient to be tested without the discomfort of prior art devices and in particular, without the use of painful massive injections.

It is another object of the invention to provide an allergen testing device using galvanometric skin response that is interfaced with a personal computer to allow the testing physician to view the real time responses of the patient on the computer screen during exposures to different substances.

It is a further object of the invention to provide an allergen testing device using galvanometric skin response wherein a series of allergens is delivered transcutaneously by an electrode.

It is still a further object of the invention to provide an allergen testing device using galvanometric skin response that allows for the storage of the test data in storage memory of a personal computer and printout of the same data for reference by the physician and patient.

Finally it is a general goal of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENT

The present invention is an allergen tester that utilizes the galvanometric response of the skin to ascertain the severity of a patient's reaction to various substances. It has been observed through clinical observation that the human body loses energy when exposed to substances that induce an allergic or otherwise detrimental reaction. This energy loss is very rapid and can be measured in microvolts. Thus, the present invention is a system that seeks to use this phenomenon to allow the physician to see, graphically, and in real time, the degree of a patients sensitivity to a given substance at the time of testing.

Figure 1:
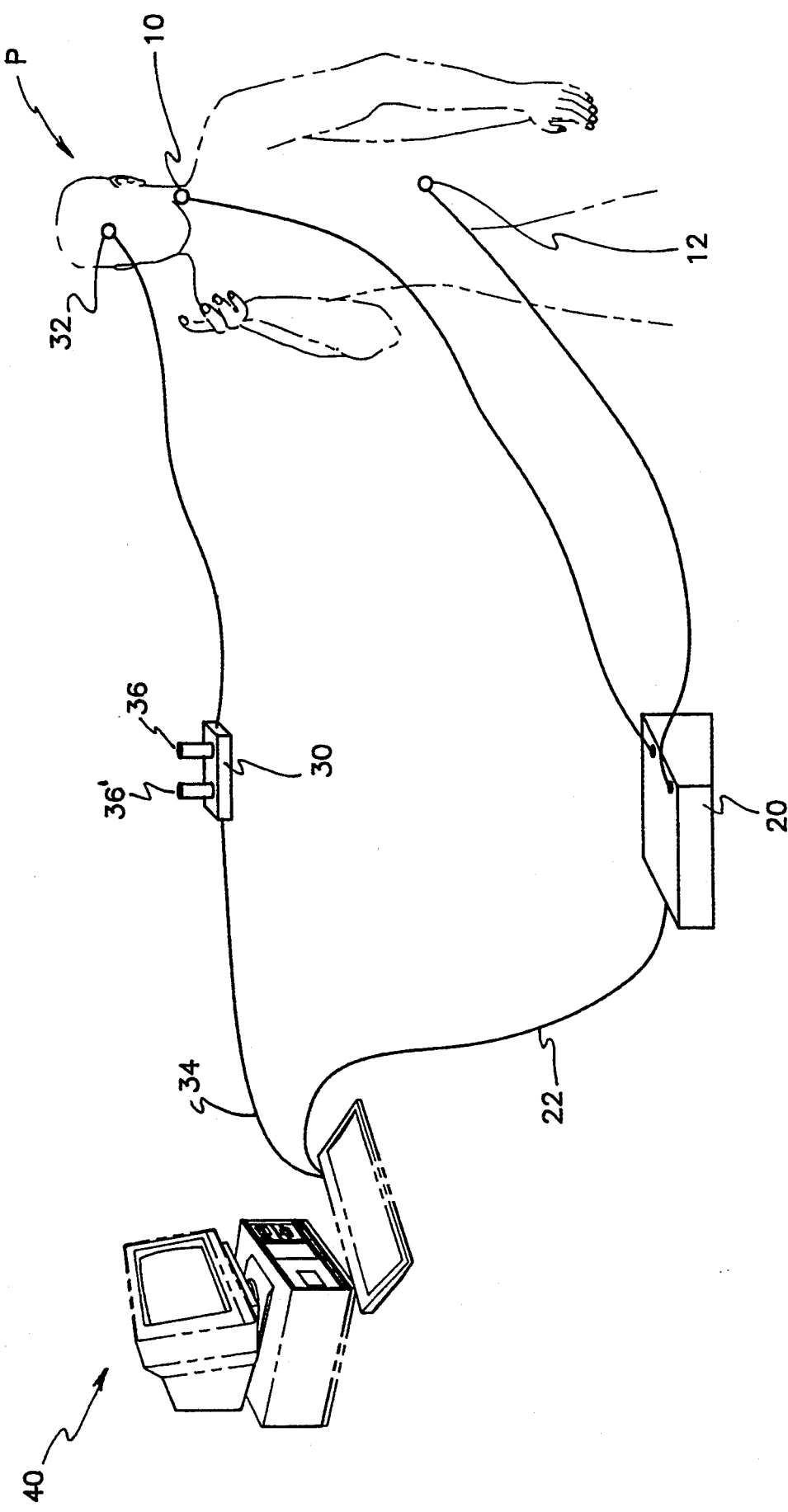
FIG. 1 is a diagrammatic view of a patient attached to the inventive device.

Referring to FIG. 1 there is seen a patient P, a first electrode 10, a second electrode 12, signal amplification and interface box 20, allergen sample tray 30, allergen delivery electrode 32, signal interface wire 22, allergen storage tray interface wire 34, and a personal computer 40. The personal computer 40 would be any of the now ubiquitous devices on the market, but preferably would be one of the type employing a high speed processor for quick operation.

The two electrodes 10, 12 are placed on the patient P's body in any convenient location. In the figure shown here, the electrode 10 is placed on the patient P's head or neck region and the electrode 12 is placed on the hip region.

The unit would first be activated and a galvanometric baseline would be established. It should be noted that though no power means are shown, both the allergen sample tray 30 and the signal amplification and interface box 20 could be powered by standard household or commercial AC current through a variety of well known means, or, by virtue of the fact that the entire system would not draw much power, they could be operated off the switchable power supply already present in the computer. In any case, the means to power the units would be available and obvious to a skilled person. The allergen delivery electrode 32 is now affixed to the patient P. A method of delivering allergens transcutaneously is disclosed in U.S. Pat. No. 4,809,707, discussed above, and is hereby incorporated by reference.

Figure 2:
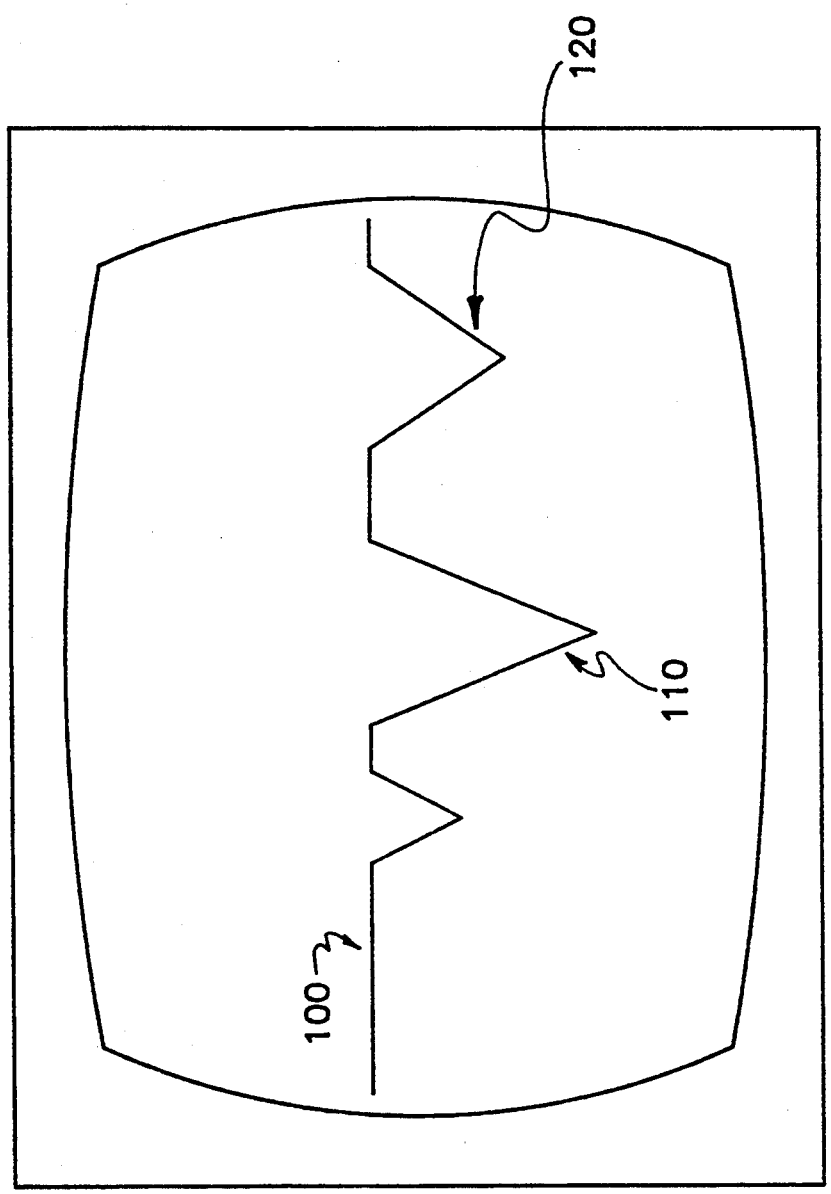
FIG. 2 is an example of the display generated by the contemplated software on a personal computer screen or, alternatively, in a printout for hard copy reference.
Figure 3:
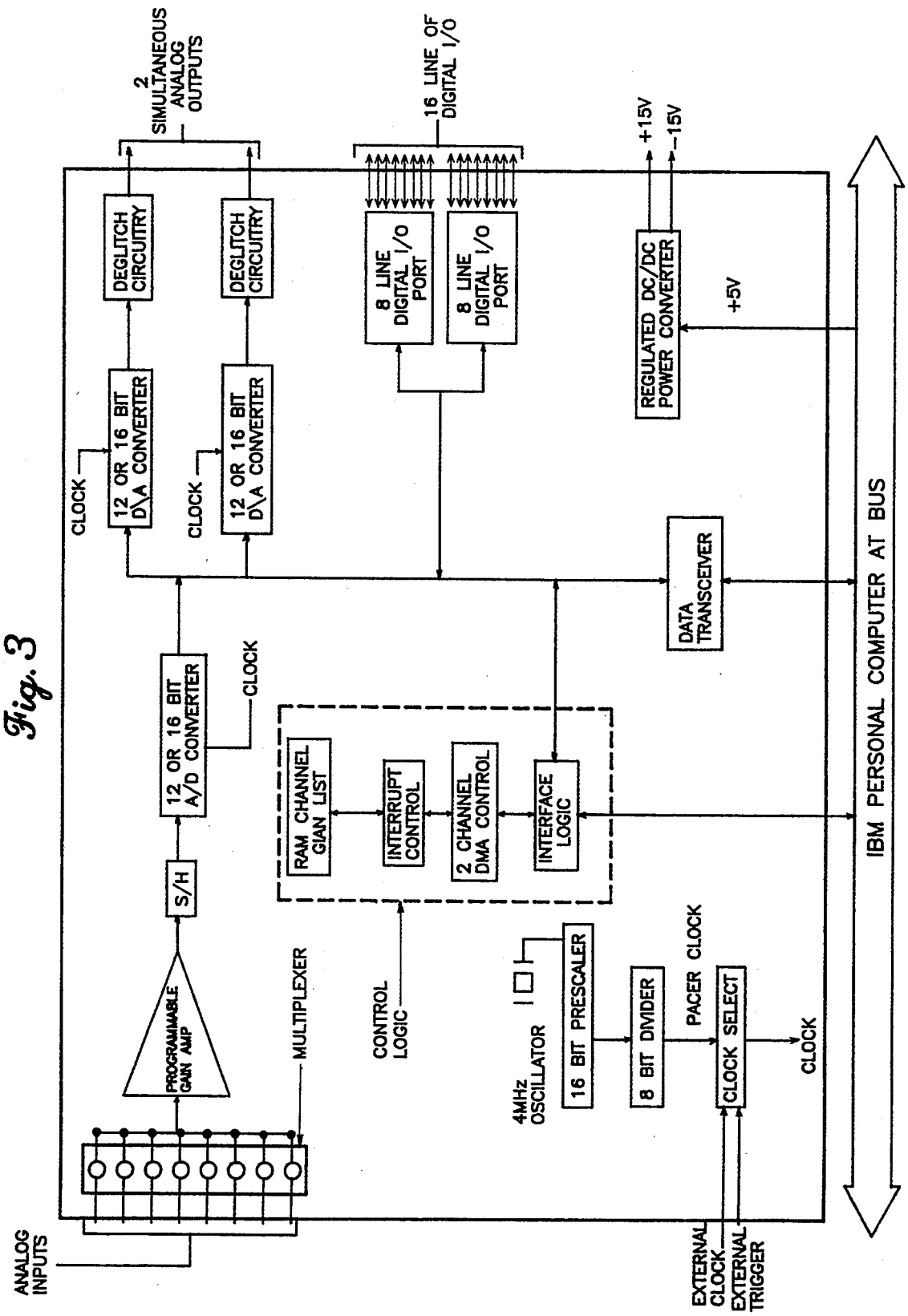
FIG. 3 is a block diagram showing the electronic signal processor used in the instant invention.

As the allergen is delivered, the response from the electrodes 10, 12 is monitored. If the patient P has no reaction to the substance the line on the monitor will resemble a flat horizontal line such as that at indicated at 100 in FIG. 2. It should be mentioned here that the means of turning the sequential microvolt A changes in the electrodes 10, 12 as measured over time (indicated by the arrow A1 in FIG. 2) into the Cartosian typo display shown in FIG. 2 are well known, and it is not deemed necessary to discuss the techniques in the present document. The details of the amplification and interface box are shown in FIG. 3 and it would be obvious to a skilled artisan how to construct such a device. Returning to FIG. 2, if the patient reacted to the substance, the graph would drop as the skin response changed, as is seen at the portion of the graph marked 110 in FIG. 2. The recovery slope 120 in the same figure shows the energetic flexibility or "bounce back" of the patient from the substance. The greater the drop in the graph, the more severe the reaction. Thus, it is contemplated that, through the allergen storage tray 30 and the allergen storage tray interface wire 34, a variety of different substances could be delivered in sequence through the allergen delivery electrode 32 by computer controlled signals that would switch to different storage sites 36, 36' within the allergen storage tray 30 for the delivery of the substance to the delivery electrode 32. This would quickly and easily give the physician the ability to ascertain the substances that the patient needed to avoid or be given immunotherapy for exposure thereto. Plots or printouts (not shown) could be generated for reference by the software contemplated in the invention. Additionally, records could be kept in the long term memory storage (not shown) of the computer 40 to provide comparisons over the course of treatment.

The following is a list of the elements discussed in the above specification:

| patient | P |
| first electrode | 10 |
| second electrode | 12 |
| signal amplification and interface | 20 |
| allergen sample tray | 30 |
| allergen delivery electrode | 32 |
| signal interface wire | 22 |
| allergen storage interface wire | 34 |
| personal computer | 40 |
| flat horizontal graph line | 100 |
| reaction drop on graph | 110 |
| recovery slope on graph | 120 |
| first allergen storage site | 36 |
| second (separate) allergen storage site | 36' |

From the foregoing description, one skilled in the art can easily ascertain the essential characteristics of this invention and, without departing from the spirit and scope thereof, can make various changes and modifications of the invention to adapt it to various usages and conditions. For example, the artisan could easily determine various other methods of administering miniscule amounts of allergy producing agents for the purpose of monitoring galvanic response recovery rates.

It is to be understood that the present invention is not limited to the sole embodiment described above, but encompasses any and all embodiments within the scope of the following claims:

It is to be understood that the present invention is not limited to the sole embodiment described above, but encompasses any and all embodiments within the scope of the following claims.

I claim:

1. A testing apparatus to test a patient's sensitivity to a plurality of potential allergens comprising:
   electrode means for measuring directly the galvanometric response of the patient, said electrode means comprising a pair of electrodes attached at different points to said patient and said electrodes being each connected to a signal amplification means;
   computer interface means included in said signal amplification means for the display and storage of said amplified signals over time in a graphic format for indicating directly the galvanometric response of said patient to each allergen in sequence; and
   allergen storage tray means containing different allergens located at different storage sites therein;
   means comprising a third electrode to introduce allergen samples transcutaneously in sequence from said allergen storage tray means by computer controlled signals into contact with said patient; whereby
   as each allergen is introduced into contact with the patient, the galvanometric response of the patient is monitored through said electrode means such that the severity of the reaction of the patient to each allergen can be determined.

2. The apparatus according to claim 1, wherein said interface means includes means to store said amplified signals digitally in long term storage.

3. A method of testing a patient's sensitivity to a plurality of potential allergens comprising the steps of:
   placing electrode means comprising a pair of electrodes adapted to receive the galvanometric responses produced by the patient at different sites on the body;
   introducing by way of a third electrode allergen samples transcutaneously in sequence from an allergen storage tray means containing allergens located at different storage sites thereon into contact said patient;
   amplifying the galvanometric responses;
   converting the galvanometric responses into a digital form;
   displaying the converted signal graphically as a function of time, whereby over time, during exposure to the allergen, the galvanometric response of the patient can be observed;
   interpreting the galvanic response as a function of time observations as an allergen sensitivity quantity.

4. The method claimed in claim 3 wherein after said displaying step the following step is performed:
   storing said digital signal data onto magnetic media.

* * * * *

UNITED STATES PATENT AND TRADEMARK OFFICE
CERTIFICATE OF CORRECTION

PATENT NO. : 5,413,113
DATED : May 9, 1995
INVENTOR(S) : Robert D. Milne

It is certified that error appears in the above-identified patent and that said Letters Patent is hereby corrected as shown below:

Title page, item (54), title, should read --ELECTRONIC ALLERGO-
& Col. 1;                                  SENSITIVITY TEST DEVICE--

Signed and Sealed this

Second Day of January, 1996

Attest:

BRUCE LEHMAN

Attesting Officer    Commissioner of Patents and Trademarks